(12) United States Patent
Batzinger et al.

(10) Patent No.: US 6,591,680 B2
(45) Date of Patent: Jul. 15, 2003

(54) SYSTEM AND METHOD FOR ULTRASONIC IMMERSION INSPECTION OF COMPONENTS

(75) Inventors: Thomas James Batzinger, Burnt Hills, NY (US); Francis Alexander Reed, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,847

(22) Filed: Jun. 15, 2001

(65) Prior Publication Data

US 2002/0189359 A1 Dec. 19, 2002

(51) Int. Cl.⁷ .............................................. G01N 29/28
(52) U.S. Cl. .............................. 73/598; 73/627; 73/644
(58) Field of Search ........................ 73/588, 597, 598, 73/599, 600, 620, 624, 625, 627, 628, 629, 644

(56) References Cited

U.S. PATENT DOCUMENTS

| | | | | |
|---|---|---|---|---|
| 4,059,098 A | * | 11/1977 | Murdock | 600/437 |
| 4,069,083 A | | 1/1978 | Palmer | 156/329 |
| 4,559,827 A | | 12/1985 | Kupperman et al. | 73/644 |
| 5,014,711 A | * | 5/1991 | Nagasaki | 600/443 |
| 5,509,420 A | | 4/1996 | Ohtomo et al. | 600/445 |
| 5,585,565 A | * | 12/1996 | Glascock et al. | 73/622 |
| 5,684,252 A | | 11/1997 | Kessler et al. | 73/618 |
| 5,729,508 A | | 3/1998 | Baker et al. | 367/176 |
| 5,796,003 A | * | 8/1998 | Sandhu et al. | 73/603 |
| 6,039,694 A | | 3/2000 | Larson et al. | 600/459 |
| 6,085,591 A | * | 7/2000 | Mallard | 73/627 |

FOREIGN PATENT DOCUMENTS

JP  61292552 A  * 12/1986  .......... G01N/29/04

OTHER PUBLICATIONS

Robert C. McMaster, "Nondestructive Testing Handbook", "Ultrasonic Test Principles", The Ronald Press Company, New York, In Two vols. II, Section 43, (1959).
Robert C. McMaster, "Nondestructive Testing Handbook", "Ultrasonic Immersion Tests", The Ronald Press Company, New York, In Two vols. II, Section 46, (1959).
J. Krautkramer, H. Krautkramer, "Ultrasonic Testing of Materials", "The Probes", Springer—Verlag Berlin, New York, pp.219–228, (1977).

* cited by examiner

*Primary Examiner*—Helen Kwok
*Assistant Examiner*—Rose M. Miller
(74) *Attorney, Agent, or Firm*—Penny A. Clarke; Patrick K. Patnode

(57) ABSTRACT

A system and method that allows for the immersion ultrasonic inspection of test samples that cannot be immersed in a fluid (e.g., water) bath. A test sample is encapsulated in a sealed evacuated bag made of nonporous flexible material. A portion of the nonporous flexible material is in contact with the surface area of the test sample where the ultrasound wave or beam will impinge. Then the sealed bag with test sample inside are immersed in an acoustic coupling medium, as is an ultrasonic transducer. The transducer is directed to transmit an interrogating ultrasound wave or beam through the vacuum bag into the component being inspected at the area of interest. The sealed bag prevents contact between the inspected component and the acoustic coupling medium.

26 Claims, 2 Drawing Sheets

SYSTEM AND METHOD FOR ULTRASONIC IMMERSION INSPECTION OF COMPONENTS

BACKGROUND OF INVENTION

This invention generally relates to systems and methods for ultrasonic inspection of products of manufacture. In particular, the invention relates to systems and methods for ultrasonic inspection of manufactured components immersed in an acoustic coupling medium.

Ultrasonic testing is a common method for evaluating the integrity and quality of components. This technique requires a method for coupling the ultrasonic wave energy from a transducer into the component being inspected. One way to couple the ultrasonic wave energy into the component is to immerse the component in a bath of a suitable acoustic coupling medium, such as water. This method has been used widely for inspecting aerospace components.

Ultrasonic inspection of integrated circuits, capacitors, and other electronic components has been utilized for years. In part, the broad use of this technique is based on the fact that ultrasonic inspection is non-destructive. Delaminations within the electronic components, especially integrated circuits, or other anomalies affecting internal electrical leads, are the usual subjects of this form of inspection. One hundred percent inspection is desirable because incomplete electrical connections within a component cannot be seen and may render the component unusable.

Coupling an ultrasonic wave or beam to an electronic component usually requires a liquid medium for inspection of electrical connections within that component; in air or other gaseous media, losses for the ultrasonic signal are often too great. In many known ultrasonic inspection systems the component requiring inspection is immersed in a tank of water or some other liquid coupling medium. This technique is well suited for imaging internal structures in components due to the uniform coupling of ultrasonic wave energy into the component.

Some components, due to their design and manufacture, cannot be immersed in a fluid. In particular, often it is not acceptable to get the test sample wet. For example, moisture in an electronic component could cause that component to fail in operation. The key to evaluating such an electrical component is to keep it dry.

The prior art for inspecting components that cannot come in contact with water was to paint the surfaces of the component prior to immersion inspection. This method is often undesirable. Cleaning the paint from the surfaces of the test sample, following inspection, is difficult. Paint that remains on the surface of the component may also hinder the usefulness of the component. In the case of some electrical components, the component would be damaged by contact with most fluids including paint.

Thus there is a need for a method of ultrasonic immersion inspection whereby the component being inspected is not exposed to moisture.

SUMMARY OF INVENTION

The present invention is directed to a technique that allows for the immersion ultrasonic inspection of test samples that cannot be immersed in a fluid (e.g., water) bath. In accordance with the preferred embodiment of the invention, a test sample is encapsulated in a vacuum bag before it is immersed in the fluid. Air will greatly affect the quality of the ultrasonic evaluation. Therefore, using a vacuum pump, the air is removed from the bag so that, when the vacuum bag is immersed in fluid, the ultrasonic wave energy can couple from the fluid through the vacuum bag into the component without traveling through an intervening air gap.

In one aspect, the invention encompasses a method for ultrasonic inspection of a test sample, comprising the steps of: enclosing a test sample within nonporous flexible material, with a portion of the nonporous flexible material being in contact with (i.e., with no air gap present} a surface area of the test sample; immersing the enclosed test sample in an acoustic coupling medium; and transmitting ultrasound wave energy from a location in the acoustic coupling medium toward the surface area of the test sample. The surface area where the ultrasound wave or beam impinges will be a function of the location of the source of the ultrasound wave energy and the location of the particular portion of the test sample being inspected.

The invention is further directed to a system for ultrasonic inspection of a test sample, comprising: a volume of an acoustic coupling medium; an enclosure made of nonporous flexible material immersed in the acoustic coupling medium; a test sample enclosed inside the enclosure with a portion of the nonporous flexible material being in contact with a surface area of the test sample; and an ultrasonic transducer immersed in the acoustic coupling medium. Optionally, the transducer can be mounted on an electromechanical scanning apparatus. The scanning apparatus may be controlled by a computer program for causing the transducer to scan the test sample along a predetermined scanning path.

In accordance with the preferred embodiments of the invention, the fluid is water, the test sample is an electrical component, and the nonporous flexible material is rubber, kapton, polyethylene or acrylic. Other nonporous flexible materials can be used provided that the material has acceptable acoustic impedance.

DETAILED DESCRIPTION

Figure 1:
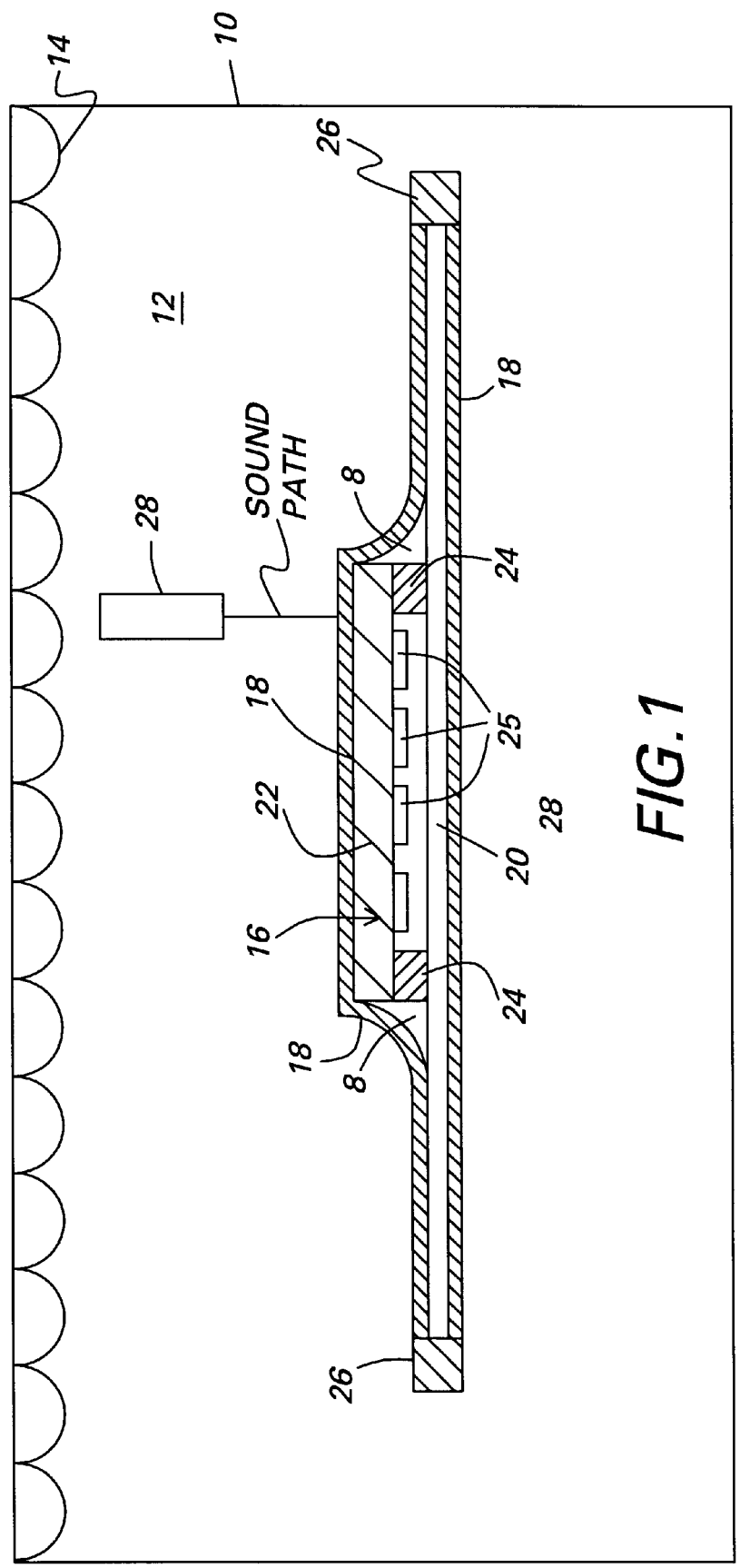
FIG. 1 is a schematic showing a test setup for ultrasonic inspection of a vacuum-packed component immersed in fluid in accordance with one preferred embodiment of the invention.

In accordance with the preferred embodiments of the invention, immersion ultrasonic inspection is carried out in a fluid bath. FIG. 1 shows a fluid bath comprising a tank 10 at least partially filled with an acoustic coupling medium 12, such as water. The water line is indicated by reference numeral 14.

The preferred embodiment further comprises a manufactured component 16 encapsulated in an evacuated bag 18 (indicated by hatched areas in FIG. 1) made of nonporous flexible material. In accordance with the preferred embodiment, the manufactured component 16 is an electrical component comprising a substrate 20 and a glass plate 22 affixed to the substrate 20 by areas of epoxy application indicated by reference numeral 24. Preferably the epoxy is applied along a continuous periphery of the bottom surface of the glass plate 22, forming a sealed volume between the substrate 20 and the glass plate 22. A multiplicity of chips (or elements) 25 are mounted to the bottom surface of the glass plate 22 and are housed within the sealed volume, as shown in FIG. 1.

In accordance with the preferred embodiment of the invention, a polyethylene vacuum bag material can be used to encapsulate the test component during the inspection process. Air is evacuated from the vacuum bag, using a vacuum pump (not shown), to ensure there is intimate contact between the vacuum bag and the test component, at least over the component surface area where the interrogating ultrasound wave or beam will impinge on the component. Intimate contact between the vacuum bag and the test sample is required for proper transmission of ultrasound into the test sample. More specifically, in the case where the immersed component will be scanned, the vacuum bag must contact the entire surface area of the component where the scanned ultrasound wave or beam impinges on the component, with no air gap between the bag material and the component surface. Otherwise the difference in acoustic impedance at an air/solid interface will cause reflection of a portion of the transmitted wave energy as well as refraction of wave energy which is not reflected.

In accordance with the preferred embodiments of the invention, the encapsulating material is a nonporous flexible material which, when evacuated, wraps against and substantially conforms to the shape of the component surface. Preferred encapsulating material includes, but is not limited to, rubber, kapton, polyethylene or acrylic. Other nonporous flexible materials having suitable acoustic impedance can be used.

In accordance with one preferred embodiment of the invention, the component is encapsulated by placing the component inside a thin bag of encapsulating material; sealing the encapsulating material (e.g., by heat or ultrasonic bonding) along the periphery of the component, leaving a passageway for connection to the vacuum pump; evacuating the interior of the sealed encapsulating material using a vacuum pump; and then sealing the passageway to maintain the vacuum inside. The vacuum bag with test sample sealed inside are then immersed in an acoustic coupling medium 12, e.g., water, at an ultrasonic scanning facility. FIG. 1 shows the test component 16 encapsulated in a vacuum bag 18 as required to perform ultrasonic inspection. The aforementioned seals, which maintain the vacuum inside the bag, are indicated by numerals 26.

Figure 2:
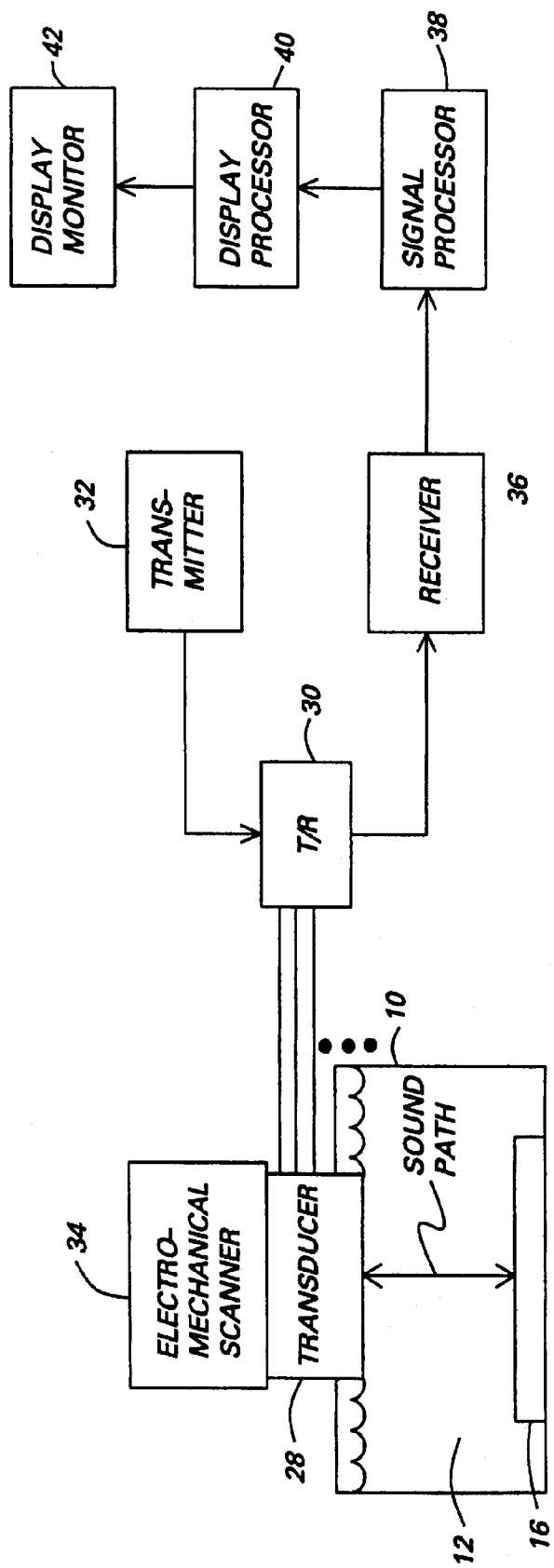
FIG. 2 is a block diagram generally depicting one example of an ultrasound imaging system suitable for scanning and imaging an immersed component enclosed in an evacuated bag in accordance with the preferred embodiment of the invention.

The test setup shown in FIG. 1 further comprises an ultrasonic transducer 28 which is immersed in the acoustic coupling medium 12 and directed toward the portion of the component 16 to be ultrasonically inspected. As previously mentioned, steps have already been taken to ensure that there is no air gap between the encapsulating material and the surface of the portion of the component to be inspected. As shown in FIG. 2, the ultrasonic transducer 28 may comprise an array of aligned piezoelectric elements which are activated in timed sequence by a transmitter 32, via transmit/receive switches 30 set in accordance with a transmit mode, to transmit a dynamically focused ultrasound beam. The transmitter 32 comprises a memory for storing the transmit beamforming time delays and pulsing circuits for pulsing the transducer elements at times dictated by the stored transmit beamforming time delays. Alternatively, the transducer may comprise a single crystal of fixed geometry with a curved lens to provide focusing of the transmitted ultrasound wave energy.

In accordance with the preferred embodiment shown in FIG. 2, the ultrasound wave energy returned from the component 16 is converted into electrical receive signals by the transducer elements of transducer array 28. In a receive mode, the transmit/receive switches 30 are set so that the electrical receive signals from individual transducer elements are sent to respective channels of a receiver 36. The individual receive channel signals are beamformed by receiver 36, in accordance with stored receive beamforming time delays, to produce a net receive signal derived from acoustic reflections from a particular focal zone. Alternatively, if the transducer is a single crystal of fixed geometry, then the returned ultrasound wave energy is converted into an electrical receive signal without beamforming.

In the case of a phased-array transducer, the test sample can be scanned by dynamically focusing the transmit and receive beams at various focal points along a transverse line at each one of a multiplicity of longitudinal positions, the transducer being physically moved at longitudinal increments. This can be accomplished by mounting the transducer array 28 on a carriage of an electromechanical scanning system 34. The scanning system may be under computer control. At each longitudinal increment, the test sample can be scanned using dynamic focusing techniques previously described. The beamsummed receive signals for a multiplicity of successive transmits at different points are each processed by a signal processor 38, which provides electrical signals representing the amplitudes of the acoustic reflections at the different points. These amplitudes are in turn sent to a display processor 40, where the data is converted into an appropriate format for display by a display monitor 42.

As should be apparent to a person skilled in the art of ultrasonic detection, dynamic transmit and receive beamforming would not be used in the case of a single crystal of fixed geometry. Instead, scanning would be accomplished by physically scanning the single-crystal transducer over an area and then detecting the reflection produced following each transmit with the same transducer.

In the inspection example shown in FIG. 1, the epoxy joint 24 in an electronic component 16 requires an ultrasonic inspection to determine the integrity of the bond. The component is of the type that cannot be immersed in water without being damaged. In accordance with the preferred embodiment, an ultrasonic inspection of the epoxy joint can be performed through the vacuum bag using the ultrasound imaging system shown in FIG. 2. For example, the acoustic reflection amplitude acquired along a scanning line can be displayed as a graph with amplitude along a vertical axis and linear position along a horizontal axis. Such a graph would display relatively lower-amplitude data in the region of the epoxy joint. This is expected due to the epoxy layer allowing for the transmission of ultrasound into the substrate. Also clearly visible in this data would be the relatively higher-amplitude data caused by the small gap in the vacuum bag material around the glass plate, as indicated by reference numeral 8 in FIG. 1. Similarly, delamination of the epoxy layer 24 from either the substrate 20 or the glass plate 22 would produce relatively higher-amplitude acoustic reflection data, as compared to the data acquired in the absence of epoxy delamination.

The technique of using a vacuum bag has been proven to be a very effective method to allow the immersion inspection of test samples while keeping the test sample dry and uncontaminated by the acoustic coupling medium, in particular, water. This technique makes use of active methods (such as a vacuum pump attached to the vacuum bag during the inspection process) to evacuate the air contained in a vacuum bag prior to immersing the test setup in water for inspection.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method for ultrasonic inspection of a test sample, comprising the steps of:

placing a test sample in a vacuum bag;

evacuating the interior of said vacuum bag with said test sample inside;

sealing said vacuum bag to maintain an evacuated state inside said vacuum bag;

immersing said evacuated vacuum bag with test sample in a volume of fluid; and transmitting ultrasound wave energy from a location outside said vacuum bag toward a portion of said test sample inside said vacuum bag.

2. The method as recited in claim 1, wherein said test sample comprises an electrical component.

3. The method as recited in claim 2, wherein said electrical component comprises a glass plate adhered to a substrate by a layer of epoxy.

4. The method as recited in claim 1, wherein said fluid is water.

5. The method as recited in claim 1, wherein said vacuum bag is made of nonporous flexible material.

6. The method as recited in claim 1, further comprising the step of immersing an ultrasonic transducer in said volume of fluid, wherein said step of transmitting ultrasound wave energy is performed by electrically activating said ultrasonic transducer while it is immersed in said fluid.

7. The method as recited in claim 1, further comprising the step of detecting the ultrasound wave energy after its impingement on and interaction with said portion of said test sample.

8. The method as recited in claim 7, wherein said detecting step comprises detecting ultrasound wave energy returned from said portion of said test sample.

9. A system for ultrasonic inspection of a test sample, comprising:

a container at least partially filled with fluid;

a sealed evacuated bag having a test sample inside, said bag being immersed in said fluid in said container; and an ultrasonic transducer immersed in said fluid in said container and positioned to transmit ultrasound wave energy toward a portion of said test sample.

10. The system as recited in claim 9, wherein said test sample comprises an electrical component.

11. The system as recited in claim 10, wherein said electrical component comprises a glass plate adhered to a substrate by a layer of epoxy.

12. The system as recited in claim 9, wherein said fluid is water.

13. The system as recited in claim 9, wherein said vacuum bag is made of nonporous flexible material.

14. The system as recited in claim 13, wherein said nonporous flexible material is rubber.

15. The system as recited in claim 13, wherein said nonporous flexible material is kapton.

16. The system as recited in claim 13, wherein said nonporous flexible material is polyethylene.

17. The system as recited in claim 13, wherein said nonporous flexible material is acrylic.

18. A method for ultrasonic inspection of a test sample, comprising the steps of:

enclosing a test sample within nonporous flexible material, with a portion of said nonporous flexible material being in contact with a surface area of said test sample;

evacuating the interior of said nonporous flexible material with said test sample inside;

sealing said nonporous flexible material to maintain an evacuated state inside said nonporous flexible material;

immersing said enclosed test sample in an acoustic coupling medium; and transmitting ultrasound wave energy from a location in said acoustic coupling medium toward said surface area of said test sample.

19. The method as recited in claim 18, wherein said acoustic coupling medium is water.

20. The method as recited in claim 18, wherein said enclosing step comprises the steps of placing said test sample inside a bag made of said flexible nonporous material.

21. The method as recited in claim 18, further comprising the step of immersing an ultrasonic transducer in said acoustic coupling medium, wherein said step of transmitting ultrasound wave energy is performed by electrically activating said ultrasonic transducer while it is immersed in said acoustic coupling medium.

22. The method as recited in claim 21, further comprising the step of detecting ultrasound wave energy returned to said ultrasonic transducer from said test sample.

23. A system for ultrasonic inspection of a test sample, comprising:

a volume of an acoustic coupling medium;

an enclosure made of nonporous flexible material immersed in said acoustic coupling medium, said enclosure being evacuated and sealed;

a test sample enclosed inside said evacuated and sealed enclosure with a portion of said nonporous flexible material being in contact with a surface area of said test sample; and an ultrasonic transducer immersed in said acoustic coupling medium and positioned to transmit ultrasound wave energy toward said surface area of said test sample.

24. The system as recited in claim 23, wherein said test sample comprises an electrical component.

25. The system as recited in claim 23, wherein said acoustic coupling medium is water.

26. The system as recited in claim 23, further comprising means for detecting ultrasound wave energy returned to said ultrasonic transducer from said test sample.

* * * * *